(12) United States Patent
Rodriguez et al.

(10) Patent No.: US 7,582,290 B2
(45) Date of Patent: Sep. 1, 2009

(54) PACKAGING CELL LINE FOR DIPHTHERIA TOXIN EXPRESSING NON-REPLICATING ADENOVIRUS

(75) Inventors: Ronald Rodriguez, Glenwood, MD (US); Wasim Haider Chowdhury, Laurel, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/510,592

(22) PCT Filed: Apr. 8, 2003

(86) PCT No.: PCT/US03/10735

§ 371 (c)(1),
(2), (4) Date: Aug. 17, 2005

(87) PCT Pub. No.: WO03/087348

PCT Pub. Date: Oct. 23, 2003

(65) Prior Publication Data

US 2005/0287116 A1 Dec. 29, 2005

Related U.S. Application Data

(60) Provisional application No. 60/370,848, filed on Apr. 8, 2002, provisional application No. 60/435,138, filed on Dec. 20, 2002.

(51) Int. Cl.
*A61K 48/00* (2006.01)
(52) U.S. Cl. .................................................. 424/93.2
(58) Field of Classification Search ................ 424/93.2
See application file for complete search history.

(56) References Cited

U.S. PATENT DOCUMENTS

| | | | |
|---|---|---|---|
| 5,652,224 A * | 7/1997 | Wilson et al. ................ 514/44 |
| 5,994,128 A * | 11/1999 | Fallaux et al. ............... 435/325 |
| 6,417,002 B1 | 7/2002 | Holick et al. | |
| 6,461,869 B1 * | 10/2002 | Schwarzenberger et al. . 435/456 |
| 6,686,196 B2 * | 2/2004 | Lieber et al. ............. 435/320.1 |

OTHER PUBLICATIONS

Anderson et al., Nature, vol. 392, pp. 25-30, 1998.*
Verma, Nature, vol. 389, pp. 239-242, 1997.*
Vile et al., Gene Therapy, vol. 7, pp. 2-8, 2000.*
McNeish et al (Gene Therapy 2004, vol. 7, 1-7.*
Rodriguez et al. Proceedings of the American Association for Cancer Research 37, 346:2358, 1996.*
Kunitomi et al. Jpn. J. Cancer Res. 91:343-350, 2000.*
Einfeld et al. (Current Opinions in Molecular Therapeutics 4: 444-451, 2002).*
Ye et al. Human Gene Therapy, 11: 621-627, 2000.*
I.H. Maxwell et al., "Cancer Research", vol. 46, pp. 4660-4664 (1986).
F. Maxwell et al., "Molecular and Cellular Biology", vol. 7, No. 4, pp. 1576-1579 (1987).
T. Uchida et al., "The Journal of Biological Chemistry", vol. 248, No. 11, pp. 3838-3844 (1973).
T. Uchida et al., The Journal of Biological Chemistry, vol. 248, No. 11, pp. 3845-3850 (1973).
Peng et al., Regulated expression of diphtheria toxin in prostate cancer cells, Molecular Therapy, 2002, v. 6, No. 4, pp. 537-545.
Kimata et al., Expression of Non-ADP-Ribosylatable, Diphtheria toxin-resistant elongation factor 2 in *Saccharomyces cerevisiae* Biochemical and Biophysical Research Communications, 1999, v. 191, No. 3, pp. 1145-1151.
Blaese et al., Science, 207: 475-480 (1995).
Roth et al., Natural Medicine, 2(9): 985-991 (1996).
Khuri et al., Nature Medicine, 6(8): 879-885, (2000).
Cavazzana-Calvo et al., Sceience, 2008: 669-672, (2000).
Kay et al., Nature Genetics, 24: 257-261, (2000).
Crystal et al., Science, 270: 404-405, (1995).

* cited by examiner

*Primary Examiner*—Brian Whiteman
(74) *Attorney, Agent, or Firm*—Edwards Angell Palmer & Dodge LLP; Peter F. Corless; Jonathan M. Sparks

(57) ABSTRACT

The invention provides a packaging cell line for production of diphtheria toxin (DT) expressing, non-replicating adenovirus for use in suicide gene therapy of cancer cells, as well as production of immunotoxins. Also provided are methods for producing diphtheria toxin (DT) expressing, non-replicating adenovirus, methods for producing immunotoxins, and adenovirus and immunotoxins produced by those methods. Further provided are methods for making a cell resistant to diphtheria toxin.

10 Claims, 2 Drawing Sheets

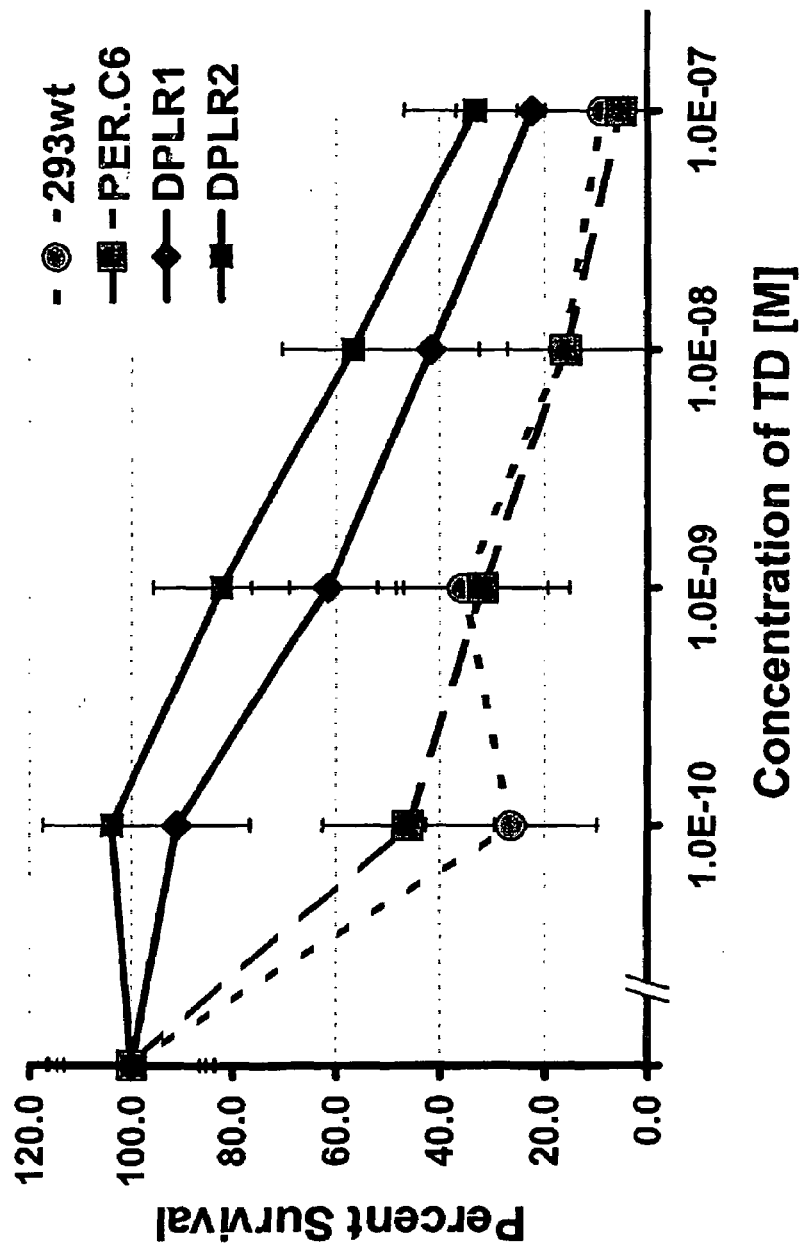

PACKAGING CELL LINE FOR DIPHTHERIA TOXIN EXPRESSING NON-REPLICATING ADENOVIRUS

RELATED APPLICATIONS

This application claims the benefit of U.S. Provisional Application Ser. No. 60/370,848, filed Apr. 8, 2002, and U.S. Provisional Application Ser. No. 60/435,138, filed Dec. 20, 2002. The entire contents of each of these applications are incorporated herein by this reference.

BACKGROUND OF THE INVENTION

Despite escalating efforts to identify antiprostate cancer agents, advanced prostate cancer is still a universally progressive and fatal disease. This unusual resistance to conventional chemotherapeutic agents has led to the exploration of a variety of novel therapeutic strategies, including suicide gene therapy (Rodriguez, R. and Simons, J. W. (1999) Urology 54:401-406). This strategy relies on the delivery to cancer cells of genes that are either directly toxic or that produce toxic metabolites when administered with a prodrug. Examples of such a strategy include herpes simplex thymidine kinase, which can phosphorylate ganciclovir (an acyclic nucleoside analogue of 2'-deoxyguanosine), into the toxic monophosphate form. Other examples include cytosine deaminase and purine nucleoside phosphorylase. Because these suicide genes poison DNA synthesis by promoting abortive DNA chain elongation, they are uniquely effective at targeting rapidly dividing cells (e.g., leukemias, lymphomas, certain childhood malignancies, and germ cell tumors). Unfortunately, because <3% of prostate cancer cells are actively dividing at any given moment, this strategy is conceptually less appealing in the context of prostate cancer (Berges, R. R. et al. (1995) Clin. Cancer. Res. 1:473-480). Thus, there is a need in the art for the development of suicide gene therapeutic agents that are active against quiescent cells (i.e., cell cycle independent), yet potent and regulated.

Diphtheria toxin (DT) is a potent cellular toxin that poisons protein synthesis by catalyzing ADP-ribosylation of elongation factor 2 (Greenfield, L. et al. (1983) Proc. Natl. Acad. Sci. USA (1983) 6853-6857) and kills cells primarily by an apoptosis-mediated pathway (Kochi, S. K. and Collier, R. J. (1993) Exp. Cell Res. 208:296-302). In certain situations (e.g., mutant p53 expression) the cells may die by necrosis rather than apoptosis; however, the pharmacokinetics is similar regardless of the pathway of cell death (Rodriguez, R. et al. (1998) Prostate 34:259-269). DT is composed of three functional domains located in two subunits, the A chain and B chain, which are joined by a disulfide bond (Bennet, M. J. and Eisenber, D. (1994) Protein Sci. 3:1464-1475). The A chain of DT has the catalytic domain, whereas the B chain comprises the receptor binding and translocation domains. It has been estimated that a single molecule of DT is capable of killing a cell (Yamaizumi, M. et al. (1978) Cell 15:245-250); therefore, strategies must be used that limit its delivery to or expression in specific target cells. These strategies have included delivering expression constructs directly to diseased cells by liposomal gene transfer under the control of a regulatory element or tissue-specific promoter (Vingerhoeds, M. H. et al. (1996) FEBS Lett. 395:245-250; Konopka, K. et al. (1997) Biochim. Biophys. Acta 1356:185-197; Duzgunes, N. et al. (1999) Mol. Membr. Biol. 16:111-118; Kunitomi, M. et al. (2000) Jpn. J. Cancer Res. 91:343-350), or delivering the toxin A-chain molecules by virtue of fusion to cloned antibody fragments (Kreitman, R. J. (1999) Curr. Opin. Immunol. 11:570-578) or peptide ligands for cell-specific receptor-mediated endocytosis (Kelley, V. E. et al. (1988) Proc. Natl. Acad. Sci. USA 85:3980-3984; Arora, N. et al. (1999) Cancer Res. 59:183-188; Hall, P. D. et al. (1999) Leukemia (Baltimore) 13:629-633).

Previous attempts at limiting toxicity of DT-A by use of a tissue-specific promoter have led to variable results. For example, Maxwell et al. (Maxwell, I. H. et al. (1986) Cancer REs. 46:4660-4664) used a truncated form of the metallothionein promoter to demonstrate that basal expression of this promoter, even in the absence of heavy metals, resulted in substantial inhibition of protein synthesis. This inhibition could be augmented by the addition of an immunoglobulin enhancer element but only minimally by cadmium. The authors were never able to demonstrate true specific cytotoxicity but rather only a preferential cell susceptibility to DT-A-mediated cell death, presumably as a result of basal expression of this highly toxic gene. As a result, subsequent efforts by this group and others concentrated on introducing an attenuated mutant of DT-A (Maxwell, F. et al. (1987) Mol. Cell. Biol. 7:1576-1579) or on tightly regulating gene expression using prokaryotic control elements (Robinson, D. F. and Maxwell, I. H. (1995) Hum. Gene Ther. 6:137-143; Paulus, W. et al. (1997) J. Neurosurg. 87:89-95). In both cases, although preferential cell killing could be demonstrated, complete abolition of nonspecific cell killing was not achieved. As a follow-up study, Keyvani et al. (Keyvani, K. et al. (1999) Life Sci. 64:1719-1724) used the same tet repressor-based system as they had reported previously with the wild-type DT-A gene with an attenuated DT-A mutant and were still unable to demonstrate complete abolition of background expression and subsequent cell death.

There currently exists a need for additional methods for producing suicide gene therapy vectors for use in killing cancer cells that are specific and reliable. The present invention fulfills that need.

SUMMARY OF THE INVENTION

The present invention is based, at least in part, on the discovery of a cell line for packaging replication deficient adenovirus that expresses diphtheria toxin subunit A (DT-A) at high titers and without contaminating replication competent adenovirus (RCA).

Accordingly, in one embodiment, the present invention provides a packaging cell line for the production of adenovirus, wherein the cell line is capable of producing adenovirus that expresses the A subunit of diphtheria toxin (DT-A) or *Pseudomonas* Exotoxin A (PEA), and wherein the cell line does not produce replication-competent adenovirus when used in conjunction with non-overlapping E1-deleted adenovirus. In an exemplary embodiment, the EF-2 gene in the cell line is mutated at codon 705, changing the glycine residue at codon 705 to arginine. Preferably, the packaging cells are resistant to about $10^{-9}$ M diphtheria toxin.

In one embodiment of the invention, the cells contain the adenovirus E1 region, e.g., the adenovirus serotype 5 (Ad5) E1-A and E1-B encoding sequences (Ad5 neucleotides 459-3510) under the control of human phosphoglycerate kinase (PGK) promoter. In a preferred embodiment, the cells are derived from PER.C6 cells.

In another embodiment, the invention provides a method of producing adenovirus which expresses the A subunit of diphtheria toxin (DT-A) or *Pseudomonas* Exdotoxin A (PEA), wherein the method does not produce replication-competent adenovirus, comprising infecting the packaging cell line of the invention with non-overlapping E1-deleted adenovirus which expresses DT-A or PEA, and culturing the cells for an amount of time sufficient to produce adenovirus. In a further embodiment the method comprises isolating adenovirus from the cells, and/or the culture medium. In a preferred embodiment, the expression of the DT-A or PEA is under the control of a tissue-specific promoter or enhancer, for example, a prostate-specific promoter or enhancer. In an exemplary embodiment, the prostate-specific promoter or enhancer comprises the first five kilobases upstream of the transcription start site of the prostate-specific antigen (PSA) gene.

In another embodiment, the present invention provides adenovirus produced by the above-described methods. In another embodiment, the invention provides a method of killing a cell (e.g., a cancer cell such as a prostate cancer cell) that is sensitive to DT-A or PEA, comprising infecting the cell with the adenovirus produced by the methods of the invention.

In another embodiment, the present invention provides a method of selectively killing a cell (e.g., a cancer cell such as a prostate cancer cell) in a subject, comprising administering a therapeutically effective amount of an adenovirus produced by the methods of the invention to the subject, wherein the tissue-specific promoter or enhancer that controls the expression of the DT-A or PEA is active only in the cell and not in other cells, thereby killing the cell but not other cells.

In another embodiment, the invention provides a method of treating a subject suffering from cancer (e.g., prostate cancer) comprising administering a therapeutically effective amount of the adenovirus produced by the methods of the invention to the subject, thereby treating said cancer.

In yet another embodiment, the invention provides a method of producing an immunotoxin comprising diphtheria toxin A or *Pseudomonas* exotoxin A, comprising contacting the packaging cell line of the invention with a nucleic acid molecule which encodes the immunotoxin, and culturing the cells for an amount of time sufficient to produce the immunotoxin. In a further embodiment, the method comprises isolating the immunotoxin from the cells and/or the culture medium. In a further embodiment, the invention provides an inmmunotoxin produced by the above-described method.

In still another embodiment, the invention provides a method of making a cell resistant to diphtheria toxin or *Pseudomonas* Exotoxin A comprising contacting a cell which is sensitive to diphtheria toxin or *Pseudomonas* Exotoxin A with a nucleic acid molecule encoding a fragment of the EF-2 protein, wherein the fragment comprises a mutation at codon 705 (e.g., a mutation from glycine to arginine), culturing the cell for a period of time sufficient to allow homologous recombination to occur between the nucleic acid molecule and the endogenous EF-2 gene, and contacting the cell with an amount of diphtheria toxin or *Pseudomonas* Exotoxin A sufficient to kill a cell which is not resistant to diphtheria toxin or *Pseudomonas* Exotoxin A, wherein growth or division of the cell in the presence of diphtheria toxin or *Pseudomonas* Exotoxin A indicates that the cell has been made resistant to diphtheria toxin or *Pseudomonas* Exotoxin A. In a preferred embodiment, the nucleic acid molecule encoding a fragment of the EF-2 protein is less than about 50, 75, 100, 150, 200, 250, 300, 350, 400, 450, 500, 550, 600, 650, 700, 750, 800, 850, 900, 950, 1000 or more nucleotides in length.

Other features and advantages of the invention will be apparent from the following detailed description and claims.

BRIEF DESCRIPTION OF THE DRAWINGS

FIG. 2 depicts a graph showing the ability of various DPL packaging cell lines to grow in the presence of DT.

DETAILED DESCRIPTION OF THE INVENTION

Figure 1:
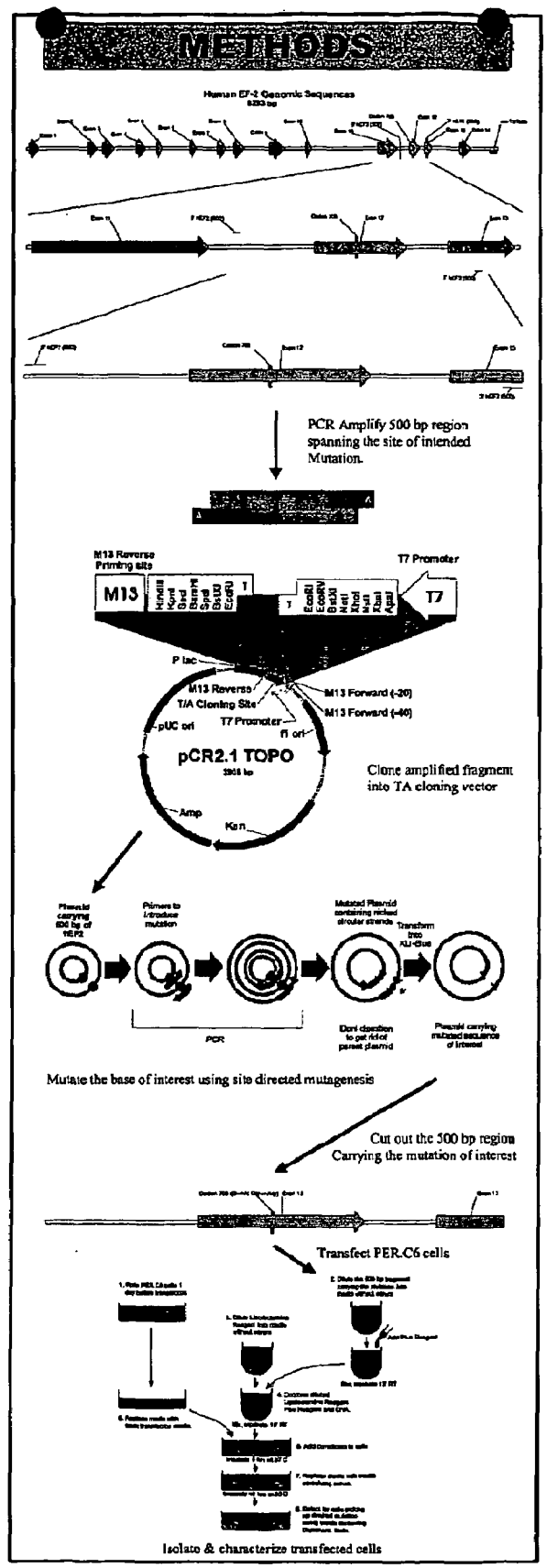
FIG. 1 depicts a schematic representation of the strategy for production of DT resistant cells.

The present invention is based, at least in part, on the discovery of a cell line for packaging replication deficient adenovirus that expresses diphtheria toxin subunit A (DT-A) at high titers and without contaminating replication competent adenovirus (RCA).

Suicide gene therapy has become an attractive strategy for cancer treatment. It relies on the delivery of genes whose products are toxic, or which produce a toxic product in conjunction with pro-drug administration. Diphtheria toxin (DT) is a potent cellular toxin that poisons protein synthesis by catalyzing ADP-ribosylation of elongation factor 2 (EF2). DT kills primarily by an apoptosis-mediated pathway. In certain situations (e.g., mutant p53 expression) the cells may die by necrosis; however, the pharmacokinetics is similar. Importantly, it kills cells in a cell-cycle independent fashion. This makes it an attractive prostate cancer therapeutic, as this malignancy tends to have a very low mitotic index.

We have generated a series of replication deficient Adenovirus (Ad) expressing the A subunit of diphtheria toxin (DT-A) driven by prostate specific promoters for use in suicide gene therapy. diphtheria toxin (DT) inhibits eukaryotic protein synthesis by ADP-ribosylating diphthamide, a post-translationally modified hidtidine residue in the EF-2 protein. DT-A causes a total shut down of protein synthesis resulting in cell death, yet the death of neighboring cells are prevented as DT-A cannot cross the cell membrane. A mutation of glycine to arginine in position 705 of the EF-2 protein gives resistance to inhibition of protein synthesis by DT. A major problem in the application of replication-defective adenovirus in gene therapy is the presence of replication-competent adenovirus (RCA), which is generated by recombination between sequences in the Ad vector and homologous Ad sequences in the helper cells. We have generated a DT resistant helper cell line, DPL, for packaging DT expressing adenovirus for suicide gene therapy, which do not make RCA. We amplified a 500 bp region from the EF-2 gene spanning the codon 705, from TSU cells. Using site directed mutagenesis we changed codon 705 from "GGA" to "AGA" to code for arginine instead of glycine. Using homologous recombination we replaced glycine with arginine in position 705 of the EF-2 protein in PER.C6 cells, and generated a DT resistant helper cell line, DPL, for packaging adenoviral vectors. These cells contain the Ad serotype 5 (Ad5) E1-A & E1-B encoding sequences (Ad5 neucleotides 459-3510) under the control of human phosphoglycerate kinase (PGK) promoter. These cells used in conjunction with non-overlapping E1-deleted adenovirus eliminates the presence of RCA in viral preps. The DPL cells are resistant to $10^{-9}$ M DT while the PER.C6 and 293 cells die within 24 hrs when exposed to $10^{-11}$ M DT. We have also verified the codon 705 mutation by southern analysis. The DPL cells used in conjunction with non-overlapping E1-deleted adenovirus eliminates the presence of RCA in viral preps, and will enable us to generate high titer DT based suicide gene therapy vectors.

Further details of the various embodiments of the invention are described in the subsections below.

I. Packaging Cell Line

In one embodiment, the present invention provides a packaging cell line for the production of adenovirus, wherein the cell line is capable of producing adenovirus that expresses the A subunit of diphtheria toxin (DT-A) or *Pseudomonas* Exotoxin A (PEA), and wherein the cell line does not produce replication-competent adenovirus when used in conjunction with non-overlapping E1-deleted adenovirus.

Human adenoviral vectors have been used extensively as gene therapy vectors. Typically, the E1 region of the vector is deleted and replaced by an exogenous nucleic acid sequence. The removal of the E1 region renders the adenovirus replication defective (Stratford-Perricaudet and Perricaudet, 1991). In the present invention, the goal is the production of adenoviruses conataining toxins, e.g., diphtheria toxin (DT-A) or *Pseudomonas* Exotoxin A (PEA). Preferably when an adenovirus containing DT-A or PEA infects a cell, it kills the cell. Such adenoviruses, referred to herein as "suicide gene therapy vectors", can be used to kill unwanted cells, e.g., cancer cells. In a most preferred embodiment, these vectors are used to kill prostate cancer cells.

The toxins, e.g., DT-A or PEA, are preferably expressed under the control of a tissue-specific promoter and/or enhancer region, which allows expression of the toxin protein only in the targeted cell or tissue type, and prevents killing of other cells. For example, in a preferred embodiment, the toxin is expressed under the control of the prostate specific antigen (PSA) promoter and enhancer, which comprises the first five kilobases upstream of the transcription start site of the prostate-specific antigen (PSA) gene (Schuur, E. R. et al. (1996) J. Biol. Chem., 271:7043; Li, Y. et al. (2002) Cancer Res. 62:2576). Use of this region restricts expression of the toxin to prostate cells, e.g., prostate cancer cells. Further tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the α-fetoprotein promoter (Campes and Tilghman (1989) Genes Dev. 3:537-546).

Diphtheria toxin (DT) is secreted from the *Corynebacterium diphtheriae* as a single polypeptide. Through proteolysis, two disulfide-linked fragments are formed: fragments A and B. DT binds to specific cell surface receptors through domains in the B fragment and is subsequently internalized by endocytosis. 12 Translocation of the catalytic A fragment in the cytosol finally results in protein synthesis inhibition by ADP ribosylation of diphthamide, a post-translationally modified histidine residue in elongation factor 2 (EF-2).13 Although some cells may not express the cell surface receptor, all mammalian cells are sensitive to DT when present in the cytosol. The extreme cytotoxicity of the wild type DT, as little as one molecule, is lethal to the cell,14. DT causes a total shut-down of protein synthesis.

*Pseudomonas* Exotoxin A (PEA) is one of the toxic proteins released by pathogenic strains of *Pseudomonas aeruginosa* (Pavlovskis, O. D. and Gordon, F. B. (1972) J. Infect. Dis. 125:631-636). It is secreted as a proenzyme with a molecular weight of 66,000 daltons (Leppla, S. A. (1976) Infect. Immun. 14:1077-1086). Like diphtheria toxin, exotoxin A is translocated into susceptible mammalian cells. Covalent alteration of the molecule occurs, rendering it enzymatically active. The intact toxin can be activated 20- to 50-fold in vitro by treatment with urea and dithiothreitol (Pavlovskis, O. D. and Gordon, F. B. (1972) J. Infect. Dis. 125:631-636; Leppla, S. A. (1976) Infect. Immun. 14:1077-1086). Exotoxin A catalyzes the transfer of the adenosine diphosphate ribose moiety of oxidized nicotinamide adenine dinucleotide onto elongation factor 2 (Iglewski, B. A. and Kabat, D. (1975) Proc. Natl. Acad. Sci. USA 72:2284-2288): NAD+EF-2→ADP-ribose-EF-2+nicotinamide+$H^+$. This ADP-ribosylation of EF-2 blocks polypeptide assembly on the surface of the ribosome (Collier, R. J. (1975) Bact. Rev. 39:54-85). As a result, this molecule is cytopathic for a number of cultured cell lines and is toxic to animals (Pavlovskis, O. D. and Gordon, F. B. (1972) J. Infect. Dis. 125:631-636; Leppla, S. A. (1976) Infect. Immun. 14:1077-1086). Although exotoxin A and diphtheria toxin have identical enzymatic activity, they exhibit distinct target cell specificities and are immunologically unrelated (Middlebrook, J. L. and Dorland, R. B. (1977) Can. J. Microbiol. 23:183-189.

Propagation of the adenovirus is accomplished through the use of packaging cell lines, also referred to herein as "helper" cell lines. As used herein, a "packaging cell line" refers to a cell line which stably expresses the E1 adenoviral region. The proteins encoded by the E1 region initiate the expression of adenoviral genes required for replication. When infected with adenovirus, the E1 region present in the cells allows the virus to replicate. 293 cells, a common laboratory cell line, are an example of a packaging cell line.

One obstacle to the production of adenoviruses containing toxin genes is that the toxin can kill the packaging cell during virus production. Accordingly, the packaging cell lines of the present invention are made resistant to both DT and PEA by the introduction of mutations in EF-2, which prevents ADP ribosylation, and thus, inactivation, of EF-2. In a preferred embodiment, EF-2 is mutated by changing codon 705 from GGA to AGA, resulting in a mutation of glycine to arginine at codon 705 in the protein. Further details of toxin-resistant mutations in EF-2 can be found in Kohno et al. (1987) J. Biol. Chem. 262:12298; and Kido et al. (1991) Cell Struct. Funct. 16:447; the contents of both of which are incorporated herein by reference. All codon and/or amino acid positions in EF-2 referred to herein correspond to the positions as described in Kohno et al. (1987) supra and Kido et al. (1991) supra. Additionally, one of skill in the art can appreciate that any other mutations in EF-2 that render it resistant to ADP ribosylation by DT or PEA are encompassed by the instant invention. Mutations can be easily tested by inducing mutations in EF-2 and determining whether the cells are resistant to DT or PEA. Preferably, cells with EF-2 mutations are resistant to about $10^{-10}$, $10^{-9}$, or $10^{-8}$ M DT.

Another problem associated with production of adenovirus using packaging cell lines is that the viral preparations can be contaminated with replication competent viruses. This results from homologous recombination between overlapping sequences from the recombinant vector and the adenovirus constructs present in the packaging cell line. Replication competent adenovirus (RCA) is generally undesirable if the adenoviral vectors are to be used in human subjects, because the virus can then replicate in an uncontrolled manner, causing undesirable side effects, including tissue damage and/or death.

The problem of RCA contamination can be solved through the use of packaging cell lines that contain an E1 region that does not contain nucleotide sequences that overlap with the nucleotides sequences of the recombinant adenovirus it is being used to propagate. Examples of packaging cell lines with preferred non-overlapping E1 regions can be found, for example, in U.S. Pat. Nos. 5,994,128, 6,265,212, 6,033,908, and 6,306,652, all of which are incorporated herein by reference. In a preferred embodiment of the invention, the cells contain the adenovirus adenovirus serotype 5 (Ad5) E1-A and E1-B encoding sequences. In a preferred embodiment, the packaging cell lines of the invention are derived from PER.C6 cells. PER.C6 cells are described in the above-referenced patents, and were also deposited at the ECACC under Accession No. 96022940.

In a preferred embodiment, the packaging cell line of the invention is derived from PER.C6 cells, in which a mutation of glycine to arginine is made in EF-2 at codon 705.

All of the embodiments of the invention (e.g., preparation of recombinant adenoviral vectors, preparation of mutated EF-2, etc.) are preferably produced by standard recombinant methods. A wide variety of molecular and biochemical methods are available for generating and expressing the vectors and constructs of the present invention; see e.g. the procedures disclosed in Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y. 1992) or other procedures that are otherwise known in the art.

II. Production of Adenovirus

In another embodiment, the invention provides a method of producing adenovirus which expresses the A subunit of diphtheria toxin (DT-A) or *Pseudomonas* Exotoxin A (PEA), wherein the method does not produce replication-competent adenovirus, comprising infecting the packaging cell line of the invention with non-overlapping E1-deleted adenovirus which expresses DT-A or PEA, and culturing the cells for an amount of time sufficient to produce adenovirus. In a further embodiment the method comprises isolating adenovirus from the cells, and/or the culture medium. In a preferred embodiment, the expression of the DT-A or PEA is under the control of a tissue-specific promoter or enhancer, for example, a prostate-specific promoter or enhancer. In an exemplary embodiment, the prostate-specific promoter or enhancer comprises the first five kilobases upstream of the transcription start site of the prostate-specific antigen (PSA) gene.

Those of skill in the art will recognize that standard methods for the production of adenovirus using packaging cells are used in the methods of the invention. Further details relating to the production of adenoviruses can be found, for example, in Li, Y. et al. (2002) supra, incorporated herein by reference. Further methods for the production of adenoviruses are found, for example, in U.S. Pat. Nos. 5,994,128, 6,265,212, 6,033,908, and 6,306,652, all of which are incorporated herein by reference.

In another embodiment, the present invention provides adenovirus produced by the above-described methods.

III. Methods of Use: Adenovirus

In another embodiment, the invention provides a method of killing a cell (e.g., a cancer cell such as a prostate cancer cell) that is sensitive to DT-A or PEA, comprising infecting the cell with the adenovirus produced by the methods of the invention. Preferably, expression of the toxin is controlled by a promoter and/or enhancer that is specific to the cell being killed. Examples of tissue specific promoters are described elsewhere herein.

In another embodiment, the present invention provides a method of selectively killing a cell (e.g., a cancer cell such as a prostate cancer cell) in a subject, comprising administering a therapeutically effective amount of an adenovirus produced by the methods of the invention to the subject, wherein the tissue-specific promoter or enhancer that controls the expression of the DT-A or PEA is active only in the cell and not in other cells, thereby killing the cell but not other cells.

In another embodiment, the invention provides a method of treating a subject suffering from cancer (e.g., prostate cancer) comprising administering a therapeutically effective amount of the adenovirus produced by the methods of the invention to the subject, thereby treating said cancer.

The preferred therapeutic methods of the invention (which include prophylactic treatment) in general comprise administration of a therapeutically effective amount of an adenovirus produced by the methods of the invention, to an animal in need thereof, including a mammal, particularly a human. Such treatment will be suitably administered to subjects, particularly humans, suffering from, having, susceptible to, or at risk for, preferably, cancer (including, but not limited, to, prostate cancer, breast cancer, lymphoma, leukemia, bone cancer, brain cancer, lung cancer, ovarian cancer, pancreatic cancer, and skin cancer). The adenoviral vectors of the invention may also be used to treat a subject with any disease or disorder in which it would be desirable to selectively kill certain cells.

For therapeutic applications, the adenoviral vectors of the invention may be suitably administered to a subject such as a mammal, particularly a human, alone or as part of a pharmaceutical composition, comprising the adenoviral preparation together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, rectal, nasal, topical (including buccal and sublingual), vaginal or parenteral (including subcutaneous, intramuscular, intravenous and intradermal) administration. The formulations may conveniently be presented using any methods well known in the art of pharmacy, provided that they are amenable to the administration of adenovirus. See, for example, *Remington's Pharmaceutical Sciences*, Mack Publishing Company, Philadelphia, Pa. (17th ed. 1985).

The adenoviruses of the invention are preferably provided to a subject, preferably a human, in a therapeutically effective amount. As used herein, a "therapeutically effective amount" is an amount sufficient to have a therapeutically beneficial effect in the subject being treated. In the context of cancer, a "therapeutically beneficial effect" includes, but is not limited to, slowing or stopping the growth of cancer cells or tumor, reduction in the number of cancer cells and/or size of the tumor, complete eradication of the cancer cells or tumor, and/or lengthening of life (e.g., prevention of death) for any amount of time.

In another embodiment, the adenoviruses of the invention may be administered in conjunction with any therapy (e.g., cancer therapy, such as chemotherapy and/or radiation) known in the art for the disease or disorder being treated.

As used herein, "treatment" of a subject includes the application or administration of a therapeutic agent to a subject (e.g., an adenovirus of the present invention), or application or administration of a therapeutic agent to a cell or tissue from a subject, who has a disease (e.g., cancer such as prostate cancer) or disorder, has a symptom of a disease or disorder, or is at risk of (or susceptible to) a disease or disorder, with the purpose of curing, healing, alleviating, relieving, altering, remedying, ameliorating, improving, or affecting the disease or disorder, the symptom of the disease or disorder, or the risk of (or susceptibility to) the disease or disorder.

IV. Immunotoxins

In yet another embodiment, the invention provides a method of producing an immunotoxin comprising diphtheria toxin A or *Pseudomonas* exotoxin A, comprising contacting the packaging cell line of the invention with a nucleic acid molecule which encodes the immunotoxin, and culturing the cells for an amount of time sufficient to produce the immunotoxin. In a further embodiment, the method comprises isolating the immunotoxin from the cells and/or the culture medium. In a further embodiment, the invention provides an immunotoxin produced by the above-described method.

Immunotoxins are toxins with altered receptor specificities. The alteration is achieved by coupling a monoclonal antibody (mAb) or growth factor to the toxin or toxin fragment. Like adenoviruses that express DT or PEA, immunotoxins comprising DT or PEA may be toxic to the cell that is used to produce them. Accordingly, the packaging cell lines of the present invention, which are DT and PEA resistant because of the EF-2 mutation, may be used to produce immunotoxins with DT and PEA in greater yields than cell lines which are not resistant to DT or PEA.

V. Methods of Making DT Resistant Cells

In still another embodiment, the invention provides a method of making a cell resistant to diphtheria toxin or *Pseudomonas* Exotoxin A comprising contacting a cell which is sensitive to diphtheria toxin or *Pseudomonas* Exotoxin A with a nucleic acid molecule encoding a fragment of the EF-2 protein, wherein the fragment comprises a mutation at codon 705 (e.g., a mutation from glycine to arginine), culturing the cell for a period of time sufficient to allow homologous recombination to occur between the nucleic acid molecule and the endogenous EF-2 gene, and contacting the cell with an amount of diphtheria toxin or *Pseudomonas* Exotoxin A sufficient to kill a cell which is not resistant to diphtheria toxin or *Pseudomonas* Exotoxin A, wherein growth or division of the cell in the presence of diphtheria toxin or *Pseudomonas* Exotoxin A indicates that the cell has been made resistant to diphtheria toxin or *Pseudomonas* Exotoxin A. In a preferred embodiment, the nucleic acid molecule encoding a fragment of the EF-2 protein is less than about 50, 75, 100, 150, 200, 250, 300, 350, 400, 450, 500, 550, 600, 650, 700, 750, 800, 850, 900, 950, 1000 or more nucleotides in length.

This invention is further illustrated by the following examples which should not be construed as limiting. The contents of all references, patents, and published patent applications cited throughout this application, as well as the figures and the Sequence Listing, are incorporated herein in their entirety by reference.

EXAMPLES

Example 1

Methods

Utilizing the 5'hEF2-500 and 3'hEF2-500 primers (see Table 1), a 500 bp region from the EF-2 gene spanning the codon 705 was PCR amplified, using genomic DNA isolated from TSU cells (a prostate cancer cell line). The amplified fragment was cloned in the pCR2.1 TOPO T/A cloning vector (Invitrogen, Carlsbad, Calif.). The cloned fragment was sequenced to verify fidelity. Using site directed mutagenesis we changed codon 705 from "GGA" to "AGA" to code for arginine instead of glycine. This was accomplished using the Quickchange kit (Stratagene, La Jolla, Calif.). The plasmid was resequenced to verify mutation. The 500 bp region was isolated by digesting the plasmid with BamHI and XbaI and running the digests on a 1% agarose gel. PER.C6 cells were transfected with the isolated DNA fragment carrying the G to A mutation, using the Lipofectamine Plus (Invitrogen). Cells were selected for the glycine to arginine in position 705 of the EF-2 mutation by growing them in the presence of diphtheria toxin (DT). Increasing concentrations of DT ($10^{-10}$ to $10^{-8}$ M) were used to isolate cells with different levels of resistance. A schematic showing the strategy for production of DT resistant cells is shown in FIG. 1.

TABLE 1

Sequence of different primers used for PCR 1) 5'hEF2-500:      5' TCCAGGCTCTAGAGGGACCTCATG 3'      (SEQ ID NO:1)
   [nt 6573-6956 of hEF2 gene]
   Amplifies 500 bp around the hEF2 codon 705

2) 3'hEF2-500:      5' AAAAGGATCCTCCTCGAACACGTGG 3'      (SEQ ID NO:2)
   [nt 7074-7060 of hEF2 gene introducing a BamHI site]
   Amplifies 500 bp around the hEF2 codon 705

3) 3'hEF2-250:      5' AAAAGGATCCAGCGGTGGGCGGGTA 3'      (SEQ ID NO:3)
   [nt 6949-6935 of hEF2 gene]
   Amplifies 387 bp around the hEF2 codon 705 used with
   5'hEF2-500.
   Used to verify the G -> A point mutation.

4) 5'hEF2QChangeG2A:  5' GACGCCATCCACCGCAGAGGGGGCCAGATCA 3'  (SEQ ID NO:4)
   5' primer for mutating hEF2 aa 705 (G -> A)
   using QuickChange 5) 3'hEF2QChangeG2A:  5' TGATCTGGCCCCCTCTGCGGTGGATGGCGTC 3'  (SEQ ID NO:5)
   3' primer for mutating hEF2 aa 705 (G -> A)
   using QhickChange Results DPL cells can grow in the presence of Diphtheria toxin: While the parent cell line, PER.C6, and 293 wt cells die at $10^{-10}$ M DT concentration, DPLR1 cells grow at $10^{-10}$ M DT, DPLR2 cells survive $10^{-9}$ M DT, and DPLR3 cells survive $10^{-8}$ M DT. DPLR1, 2, and 3 are different clonal DPL lines. See FIG. 2.

The resistance of the DPL cells is due to the mutation of the EF2 gene and not a receptor mutation: The G≧A mutation at codon 705 results in the loss of a MspA1I Restriction site. A 387 bp region spanning the site of mutation was PCR amplified and tested for the loss of MspA1I to check for the presence of the mutation.

DPL cells package replication deficient Adenovirus expressing the A subunit of diphtheria toxin (DT-A) without generating RCA: Cells were infected with 10 MOI of Ad5-CN65-DT-A and the virus was harvested after CPE was apparent (3-4 days). Packaging of the DT gene was checked for using primers against a region of DT. Presence of RCA was checked using primers against a region of the E1A promoter.

Equivalents

Those skilled in the art will recognize, or be able to ascertain using no more than routine experimentation, many equivalents to the specific embodiments of the invention described herein. Such equivalents are intended to be encompassed by the following claims.

---

What is claimed:

1. A method of killing a cell that is sensitive to DT-A or PEA, comprising infecting the cell with an adenovirus produced by a packaging cell line, wherein the adenovirus comprises an adenoviral vector comprising a promoter operably linked to a nucleic acid encoding the A subunit of diphtheria toxin (DT-A) or *Pseudomonas* Exotoxin A (PEA), and wherein the cell line is capable of producing adenovirus that expresses the A subunit of diphtheria toxin (DT-A) or *Pseudomonas* Exotoxin A (PEA), wherein the cell line does not produce replication-competent adenovirus when used in conjunction with non-overlapping E1-deleted adenovirus, wherein the cell line is resistant to DTA and PEA and wherein the cell line has a mutated human EF-2 gene that encodes an EF-2 protein that is mutated at codon 705.

2. The method of claim 1, wherein the cell is a cancer cell.

3. A method of selectively killing a cell in a subject, comprising administering a therapeutically effective amount of an adenovirus to the subject wherein the adenovirus is produced by a packaging cell line, wherein the adenovirus comprises an adenoviral vector comprising a promoter operably linked to a nucleic acid encoding the A subunit of diphtheria toxin (DT-A) or *Pseudomonas* Exotoxin A (PEA), and wherein the cell line is capable of producing adenovirus that expresses the A subunit of diphtheria toxin (DT-A) or *Pseudomonas* Exotoxin A (PEA), and wherein the cell line does not produce replication-competent adenovirus when used in conjunction with non-overlapping E1-deleted adenovirus, wherein the cell line has a mutated human EF-2 gene that encodes an EF-2 protein that is mutated at codon 705, wherein the adenovirus comprises a tissue-specific promoter or enhancer that controls the expression of the DT-A or PEA wherein the tissue-specific promoter or enhancer is active only in the cell and not in other cells, thereby killing the cell but not other cells.

4. The method of claim 3, wherein the cell is a cancer cell.

5. A method of treating a subject suffering from cancer comprising administering a therapeutically effective amount of the adenovirus to the subject, wherein the adenovirus is produced by a packaging cell line, wherein the adenovirus comprises an adenoviral vector comprising a promoter operably linked to a nucleic acid encoding the A subunit of diphtheria toxin (DT-A) or *Pseudomonas* Exotoxin A (PEA), and wherein the cell line is capable of producing adenovirus that expresses the A subunit of diphtheria toxin (DT-A) or *Pseudomonas* Exotoxin A (PEA), and wherein the cell line does not produce replication-competent adenovirus when used in conjunction with non-overlapping E1-deleted adenovirus, wherein the cell line has a mutated human EF-2 gene that encodes an EF-2 protein that is mutated at codon 705, and wherein the cell line is resistant to DTA and PEA thereby testing said cancer.

6. The method of any one of claims 1, 3, or 5, wherein the glycine residue at codon 705 of the EF-2 protein is mutated to arginine.

7. The method of claim 1, wherein the packaging cell lines are resistant to about $10^{-9}$ M diphtheria toxin.

8. The method of claim 1, wherein the packaging cell lines contain the adenovirus E1 region.

9. The method of claim 1, wherein the packaging cell lines contain the adenoviruss serotype 5 (Ad5) E1-A and E1-B encoding sequences.

10. The method of claim 1, wherein the packaging cell lines are derived from PER.C6 cells.

* * * * *

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 1
tccaggctct agagggacct catg                                              24

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 2
aaaaggatcc tcctcgaaca cgtgg                                             25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 3
aaaaggatcc agcggtgggc gggta                                             25

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 4
gacgccatcc accgcagagg gggccagatc a                                      31

<210> SEQ ID NO 5
<211> LENGTH: 31
<212> TYPE: DNA
<213> ORGANISM: Artificial Sequence
```

-continued

```
<220> FEATURE:
<223> OTHER INFORMATION: Description of Artificial Sequence: Primer

<400> SEQUENCE: 5
tgatctggcc ccctctgcgg tggatggcgt c                                      31
```